United States Patent [19]

Prichard et al.

[11] Patent Number: 5,330,449
[45] Date of Patent: Jul. 19, 1994

[54] CATHETER STRAIN RELIEF DEVICE

[75] Inventors: James B. Prichard, Hazelwood; Raymond O. Bodicky, Oakville, both of Mo.

[73] Assignee: Sherwood Medical Company, St. Louis, Mo.

[21] Appl. No.: 22,824

[22] Filed: Feb. 24, 1993

Related U.S. Application Data

[63] Continuation of Ser. No. 642,485, Jan. 17, 1991, abandoned.

[51] Int. Cl.⁵ ............... A61M 25/00; C09J 5/100
[52] U.S. Cl. ........................... 604/282; 604/283; 156/294; 156/305; 285/235; 285/915
[58] Field of Search ............... 604/164–169, 604/280–283, 284, 905, 239–240; 285/417, 114–116, 235, 21, 22, 915; 138/106, 109, 110, 120, 96 R; 156/294, 292, 295, 158, 305; 439/449

[56] References Cited

U.S. PATENT DOCUMENTS

| | | | |
|---|---|---|---|
| 1,115,908 | 11/1914 | Dees | 604/95 |
| 1,569,174 | 1/1921 | Crowther | 285/114 |
| 2,236,731 | 4/1941 | Oberly | 138/110 |
| 3,756,235 | 9/1973 | Burke et al. | 604/240 |
| 3,784,236 | 1/1974 | Slocum | 285/115 |
| 3,807,776 | 4/1974 | Bingham | 285/915 |
| 3,920,268 | 11/1975 | Stewing | 285/21 |
| 3,920,787 | 11/1975 | McDowell et al. | 285/240 |
| 4,035,002 | 7/1977 | Curtin | 285/915 |
| 4,137,117 | 1/1979 | Jones | 156/305 |
| 4,323,065 | 4/1982 | Kling | 604/283 |
| 4,581,024 | 4/1986 | Swenson | 604/240 |
| 4,610,674 | 9/1986 | Suzuki et al. | 604/282 |
| 4,614,188 | 9/1986 | Bazell et al. | 604/97 |
| 4,673,455 | 6/1987 | May | 156/305 |
| 4,819,637 | 4/1989 | Dormandy, Jr. et al. | 606/159 |
| 4,846,174 | 7/1989 | Willard et al. | 604/95 |
| 4,913,701 | 4/1990 | Tower | 606/192 |
| 4,929,235 | 5/1990 | Merry et al. | 604/167 |
| 4,946,466 | 8/1990 | Pinchuk et al. | 604/95 |
| 4,960,412 | 10/1990 | Fink | 604/167 |
| 4,998,923 | 3/1991 | Samson et al. | 604/95 |
| 5,000,611 | 3/1991 | Reinhart | 156/305 |
| 5,009,391 | 4/1991 | Steigerwald | 604/167 |

Primary Examiner—C. Fred Rosenbaum
Assistant Examiner—Mark Bockelman
Attorney, Agent, or Firm—Andrew J. Beck; Montgomery W. Smith; Gene B. Kartchner

[57] ABSTRACT

A strain relief device for use at a tube/hub junction of a tubular device such as a catheter. The strain relief device forms a lumen which may have a reduced diameter at a distal section thereof which can cooperate with the outer diameter of a catheter tube to form a wicking surface. The wicking cavity is formed to allow bonding material to be added thereto which, through capillary action, forms a uniform and controlled bond pattern between the strain relief device and the catheter tube. A catheter including the strain relief device of the invention is manufactured by inserting the strain relief device over a catheter tube/hub junction and permanently bonding the proximal end of the strain relief device to the hub in a conventional manner. The distal end of the strain relief device is then bonded to the catheter tube. The stain relief device of the present invention resists axial pulling forces, as well as bending forces, which may be applied to the catheter.

19 Claims, 3 Drawing Sheets

CATHETER STRAIN RELIEF DEVICE

This is a continuation of copending application Ser. No. 07/642,485 filed on Jan. 19, 1991 now abandoned.

BACKGROUND OF THE INVENTION

1. Field of the Invention

This invention relates generally to strain relief devices for tubular members. More specifically, this invention relates to improved strain relief devices for use at the hub/tube junction of a catheter assembly. Even more specifically, the present invention relates to improvements in strain relief devices for increasing the connection strength of a hub/tube junction of a catheter assembly.

2. Brief Description of the Prior Art

Catheters of the prior art are generally formed of three main elements. A first element is generally an elongated catheter tube (tube) which is intended to be of a sufficient length such that a distal end thereof may pass into a patient while the proximal end thereof remains outside the patient so as to allow the delivery and/or removal of fluids from the patient's body. A second element of the catheter is generally referred to as a catheter hub (hub) which is generally affixed to the proximal end of the tube to form a hub/tube junction. The hub is used to allow connection of a fluid delivery or fluid reception system to the catheter in a manner and for purposes commonly known in the prior art.

When strain relief is required between the hub and tube, the hub and tube constitute merely a subassembly of the catheter, and a strain relief device is included as a third element thereof. The strain relief device is generally attached over the hub/tube junction in such a way as to cause part of the strain relief device to be affixed to the hub while another part thereof encompasses a portion of the tube (See for example, prior art FIG. 1 of the present disclosure).

Strain relief devices of the above described type have been used in the past to prevent the collapse of a tube when it is subjected to lateral (bending) forces. The strain relief device is designed to prevent non-uniform curvature, i.e., "kinking" of the tube of the catheter at or near the hub/tube junction. Strain relief devices of this type are usually attached to a catheter at a point where the tube thereof forms a junction with the more rigid hub structure. This placement of the strain relief device prevents bending forces from concentrating at the hub/tube junction due to the non-uniform flexibility thereacross. The strain relief device is basically designed to spread bending forces along a significant length of the tube and away from the hub/tube junction.

Although strain relief devices have in the past functioned adequately to relieve the strain of bending forces at a hub/tube junction, they have nevertheless been less than adequate to aid in strengthening the junction against axial forces, i.e., forces along the longitudinal axis of the tube which tend to pull the tube away from the hub. Such axial forces can arise either during normal use, or during any number of common accidents or mishaps. Forces exceeding the strength of the hub/tube junction of the catheter can lead to failure thereof, and possibly disastrous consequences for a patient who may heavily rely on its proper functioning.

There exists therefore a need in the art to develop a strain relief device which not only functions to relieve strain at a hub/tube junction due to bending forces, but also function to relieve strain on a hub/tube junction due to axial hub/tube separation forces (axial pulling forces).

Manufacturing of prior art catheters which include a hub/tube junction has generally included either a solvent bond between the hub and the tube, or an insert molding process in which the tube is placed into a hub mold, and molten plastic is allowed to flow into the mold around the catheter to form and secure the hub to the tube.

There is ordinarily no flange, anchor, threading or other securing means used to insure a more secure connection between the tube and the hub due to significant increases in the time and expense of manufacture. As a result, the junction generally formed by the hub as it is melted about the tube is the only bond on prior art catheters which resists axial separation forces.

Inconsistencies may arise in the above molding process which may affect the ability of the molten plastic to adhere to the tube to form the bond between the hub and tube. Consequently, the bond at the hub/tube junction may be insufficiently strong to effectively resist axial separation forces. The inconsistencies may develop in the manufacturing process in several ways. For example, moisture content in the raw hub material may arise, thus inhibiting bonding between the molten plastic and the tube. Also, since many raw hub materials are hydroscopic, they often absorb and are affected by water in a way adverse to the strength of the hub/tube bond.

Further, worn molds which have been used to manufacture a large number of catheters may fit together in a less than perfect manner, allowing flash material to be formed at the parting line of the hub molds. Flash generated in certain areas of the hub of the catheter due to mold wear has been known to cause the catheter to fail prematurely when subjected to axial forces.

Other problems and/or parameters in the molding process, such as molding pressure, temperature and mold gate size also have an effect on the bond formed between the tube and the hub during manufacture.

There exists therefore a need to develop a manufacturing process which can compensate for, and even overcome, possible weaknesses in the hub/tube junction due to inconsistencies in the hub molding step of the manufacturing process.

Catheters of the above described nature are routinely manufactured in large quantities, and are routinely tested for the strength of the bond of the hub/tube junction in order to verify that a predetermined minimum allowable axial force, called a "minimum allowable pull to separation force" is met by the manufactured catheter. For reasons of safety it is critical for certain intended uses of the catheters that no single catheter of a manufactured lot fail when subjected to forces at or below this minimum allowable pull force. A test revealing a substandard catheter therefore, will cause the entire lot of catheters from which it was a part to be scraped, resulting in a significant loss of time and money to the manufacturer.

There exists therefore a further need to develop a catheter and a manufacturing process therefore in which the catheters consistently and uniformly meet minimum pull strength requirements.

OBJECTS OF THE INVENTION

It is an object of the present invention to provide a strain relief device which is capable of resisting both bending and axial forces generated at a hub/tube junction of a catheter.

It is another object of the present invention to provide a strain relief device which can be redundantly bonded about a hub/tube junction of a catheter to prevent concentration of bending forces which would tend to cause kinking of the tube, and at the same time resist axial forces which would tend to cause a separation of the tube from the hub.

It is another object of the present invention to provide a strain relief device which is symmetrically bonded to a tube of a catheter in such a manner that stresses due to axial pulling forces are evenly distributed around the tube in such a manner that premature cracking and/or failure due to uneven strain in the tube is avoided.

It is also an object of the present invention to provide a strain relief device which is capable of drawing bonding material between the strain relief device and the tube into a uniformly and symmetrically-shaped bonding cavity through capillary action.

It is another object of the present invention to provide a strain relief device as described above which provides added resistance against axial pull forces at the hub/tube junction, while at the same time maintains predetermined flexibility and deflection characteristics for resisting the concentration of bending forces at the hub/tube junction.

It is another object of the present invention to provide a strain relief device as described above which is also inexpensive and an integral part of a consistent and repeatable catheter manufacturing process.

SUMMARY OF THE INVENTION

Briefly, and in general terms, the present invention provides a strain relief device and method of manufacturing the same, which assists in resisting bending forces to avoid kinking of the tube at a hub/tube junction of a catheter, while at the same time assists in the resistance of axial pull forces between the hub and the tube to avoid separation thereof during use.

In a first preferred embodiment, by way of example and not necessarily by way of limitation, a strain relief device (device) made in accordance with the principles of the present invention includes an elongate body formed of elastomeric material having a lumen formed therethrough along its entire length. The strain relief device lumen (lumen) may be divided into proximal, central and distal sections which may each be of different and/or varying diameters. The device is placed about a hub/tube junction of the catheter in such a manner that a nose portion of the hub is located in the proximal section of the lumen of the device, and the tube passes through the central and distal lumen sections to extend beyond the distal end of the device. The distal section of the lumen may then be bonded to the tube to form a second, redundant bond between the strain relief device and the tube.

In a second preferred embodiment of the present invention, the central section of the lumen of the strain relief device as described above is formed of a diameter significantly greater than the outer diameter of the tube, and the distal section of the lumen is formed of a diameter which is only slightly greater than the outer diameter of the tube. When the strain relief device is placed about the hub/tube junction of a catheter, an elongated annular cavity is formed between the distal section of the lumen and the outer surface of the tube. The cavity is designed so that when bonding material of a predetermined viscosity is added thereinto it will be moved by capillary action to fill the cavity in a uniform, bilaterally symmetrical bonding pattern.

A distal end of the distal section of the lumen of this second embodiment of the strain relief device may be formed into a funnel-shaped opening if desired, in order to assist in the placement of bonding material adjacent to the cavity and to facilitate the flow of the bonding material around the tube and into the cavity.

A catheter including the first preferred embodiment of the strain relief device of the present invention can be manufactured by a preferred process which may include forming a hub/tube junction by insert molding a tube to a hub as described above, and then assembling the strain relief device over the tube. The lumen of the strain relief device is formed of a proximal section sized to snugly attach to the nose portion of the hub, and a central and distal section, sized to allow passage of the tube therethrough. Bonding material, such as solvent, is used to form a permanent bond between the strain relief and the tube and/or to form a bond between the strain relief and the hub.

In second preferred method of manufacture the present invention, a central section of the strain relief lumen is sized to a diameter substantially greater than the outer diameter of the tube, and contrarily, the distal section of the lumen is sized to a diameter only slightly greater than the outer diameter of the tube. The distal section of the lumen may have the distal end thereof formed into a funnel shape to assist the flow of bonding material into the cavity as described in conjunction with the first embodiment if so desired.

The tube of the catheter is then inserted through the lumen of the strain relief device and a bonding material such as a solvent is placed on the nose portion of the hub. The proximal section of the lumen of the strain relief device is then affixed to the hub nose to form a first permanent bond. More bonding material is then dispensed into the cavity through the funnel-shaped distal end of the strain relief device (if present) and allowed through capillary action to flow around the tube and into the cavity. This forms a second (redundant) permanent bond, independent and spaced apart from the first permanent bond at the nose of the hub. The formation of the central section of the lumen of the strain relief device to a diameter significantly larger than that of the distal lumen section operates to prevent bonding material from flowing away from or out of the cavity. The bonding material is held in the distal section of the lumen by the capillary forces caused by the design of the cavity.

The above and other objects and advantages of the present invention will become apparent from the following more detailed description, when taken in conjunction with the accompanying drawings in which like elements are identified with like numerals throughout.

DETAILED DESCRIPTION OF THE PREFERRED EMBODIMENTS

Figure 1:
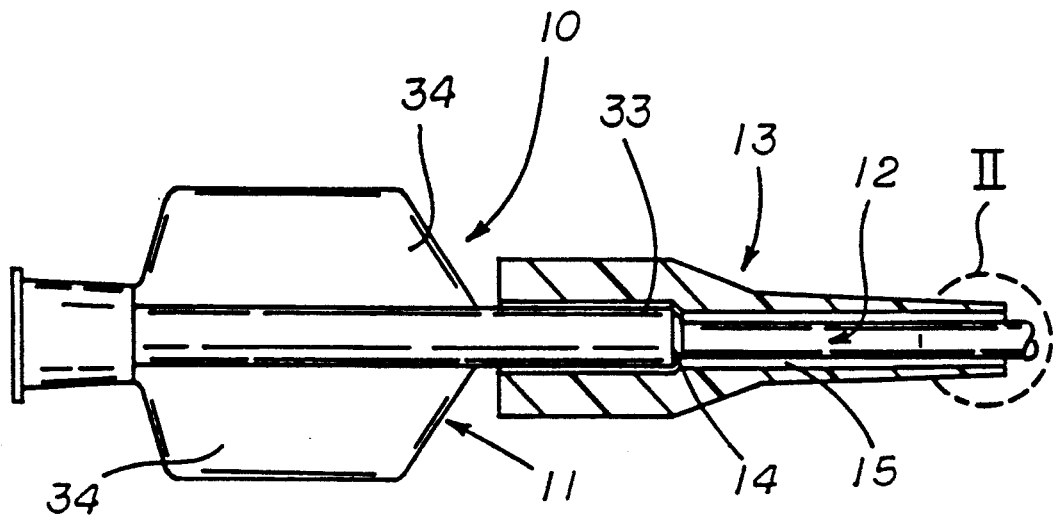
FIG. 1 shows a partial cross-sectional view of a catheter and strain relief device of a prior art configuration showing the catheter in perspective and the strain relief device in cross-section.

As shown in FIG. 1, a prior art catheter 10 including a hub 11 and a tube 12 is shown in conjunction with a cross-sectional representation of a prior art strain relief device 13.

A prior art catheter such as catheter 10 can be formed by placing a section of a tube 12 into a mold (not shown) which has been designed to form a hub 11, and allowing molten plastic material to fill the mold and surround the portion of the tube 12 inserted therein. In the molding process, molten plastic forming hub 11 will surround the proximal end of tube 12 and form a junction 14 between the tube 12 and the hub 11.

Tube 12 is usually formed of a fairly soft flexible polyurethane having a relatively low durometer hardness. Hub 11 is usually formed of a more rigid polyurethane having a lower melting point than the material used for tube 12, but a relatively higher durometer hardness. The junction 14 therefore consists of a relatively rigid material (the hub 11) adjoined with a relatively flexible material (the tube 12).

The prior art strain relief device 13 is preferably formed by an injection molding process and is formed of a material which has a flexibility which is less than that of the tube 12, yet greater than that of the hub 11. The strain relief device 13 is also formed to include a lumen 15 therethrough which is of a diameter sufficiently greater than the outer diameter of tube 12 so as to allow uninhibited passage of the tube 12 therethrough for ease of assembly.

At the proximal end of the strain relief device 13, the lumen 15 is formed to be substantially the same diameter as the outer diameter of the nose portion 33 of hub 11 which is to be inserted therein. Prior to the placement of nose 33 into the lumen 15, it is generally the practice in the prior art to place a bonding material, such as a solvent, about the nose 33 in order to insure that the strain relief device becomes permanently attached thereto when connected.

Figure 2:
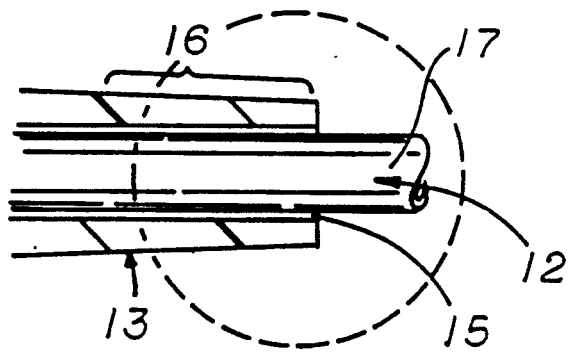
FIG. 2 is an enlarged view of the area labeled "II" in FIG. 1.

As best seen in FIG. 2, the prior art catheter tube 12 extends through lumen 15 beyond distal portion 16 of prior art strain relief device 13. As can be seen, tube 12 is allowed substantial play within the lumen 15 in order to simplify insertion of the strain relief device 13 over the tube 12 during assembly. An axial pulling force between the hub 11 and the tube 12, directed along central axis 17, would not be resisted in any manner by the prior art strain relief device 13 attached to the catheter 10 in the manner shown in FIG. 2. However, a bending forces directed laterally to axis 17 would cause tube 12 to contact the lumen 15 and would thereafter be resisted by the strain relief device 13. The strain relief device 13 is designed of a durometer hardness and of an overall geometry which provides a predetermined flexibility and deflection in response to lateral forces applied thereto as a result of the bending of tube 12. The design of device 13 is calculated to provide predetermined flexibility and deflection characteristics which operate to resist kinking or collapse of the tube 12 at the hub/tube junction 14.

Since the prior art strain relief device 13 has no effect on axial forces through tube 12, the catheter 10 (as shown in FIG. 1) will fail as a result of axial pull forces when the strength of the molded hub/tube junction 14 is overcome. The above described molding problems, such as water accumulation in the molding material, have rendered it difficult in the past to maintain uniform strength in the hub/tube junction 14 using prior manufacturing methods. Since it is extremely important (due to potentially disastrous effects of failure of a catheter to a patient) to have each and every catheter 10 meet minimum specifications, there is necessarily a low tolerance in the medical art for variations in the minimum pull strength of the hub/tube junction 14 of a catheter. Due to the high performance and reliability requirements of medical catheters, a significant amount of scrap can be generated during the prior art manufacturing process if it becomes necessary to scrap an entire lot of catheters 10 as a result of a single sample catheter from the lot failing to meet a minimum acceptable pull strength.

Figure 3:
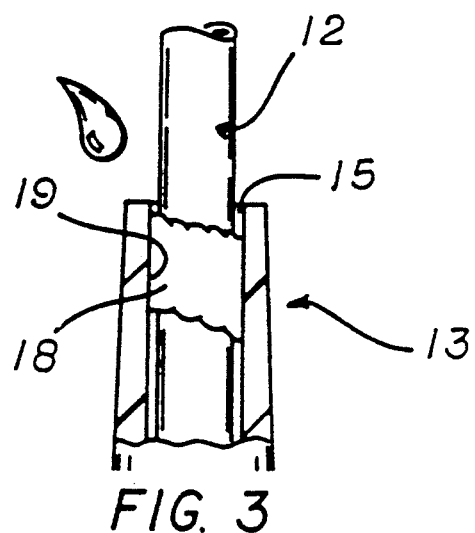
FIG. 3 is a partial cross-sectional view of a first preferred embodiment of a strain relief device of the present invention showing the flow pattern of bonding material placed in between a catheter tube and a strain relief device in accordance with the principles of the present invention, the catheter and the bonding material being shown in perspective and the strain relief device being shown in cross-section.

As shown in FIG. 3, a first preferred embodiment of the present invention includes the addition of a bonding material 18 to the lumen 15 of a prior art strain relief device 13. The bonding material 18 may be of any well known type adhesive or solvent but is preferably a solvent such as tetrahydoflourane (THF) or cyclohexanone, or other solvent type bonding materials or combinations thereof which are known to be useful for bonding polymeric materials. Further, although not elaborated on in the description of the preferred embodiments, it is anticipated by the present invention that the bond between the hub 11 and/or tube 12, and the strain relief devices be formed in any well known manner, including but not limited to, welding, friction bonding, chemical bonding (of any sort), electromagnetic wave heating, etc.

The addition of redundant bond 19 into the catheter 10 which includes prior art strain relief device 13 (as shown in FIG. 3) causes a significant increase in the axial pull strength of the catheter 10 over prior art designs.

The first embodiment of the present invention as shown in FIG. 3 increases the pull strength of devices on which it is employed in a manner which is extremely desirable for a number of applications and intended uses.

Also the first embodiment of the invention, due to the fixation of the device 13 to the tube 12, has flexibility and deflection characteristics different from those of the prior art catheter 10 and strain relief device 13 (as shown in FIG. 1). Since bending forces applied to tube 12 are resisted by the strain relief device 13 (as shown in FIG. 3) differently than the strain relief device (as shown in FIG. 1 due to the presence of the redundant bond 19 formed by the bonding material 18, the first embodiment of the present invention is better suited for particular uses than prior art devices.

Figure 4:
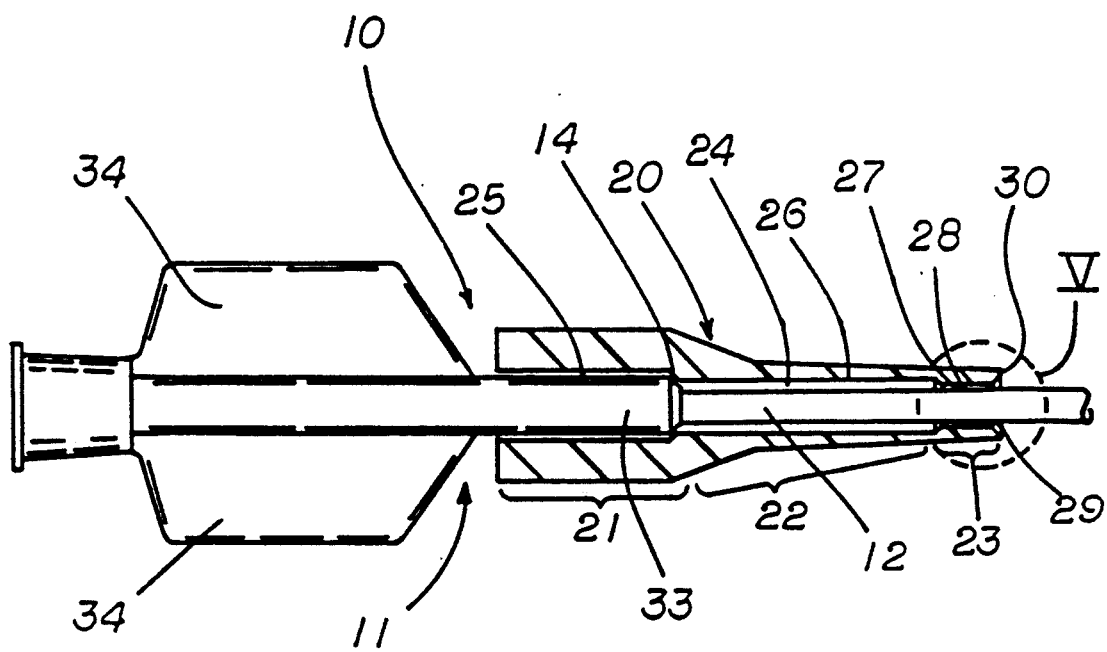
FIG. 4 shows a partial cross-sectional view of a catheter incorporating a second preferred embodiment of a strain relief device formed in accordance with the principles of the present invention with the catheter being shown in perspective and the strain relief device being shown in cross-section.

FIG. 4 shows a second preferred embodiment of the present invention which not only includes a redundant bond for increasing the pull strength of the catheter 10 in the manner as shown in FIG. 3 with respect to the first embodiment of the invention, but also includes a structural design which insures that the bond material will form into a uniform, repeatable, bilaterally symmetrical bond. Further, the second embodiment of the invention is designed to have predetermined flexibility and deflection characteristics against bending forces which take into account the presence of the redundant bond to inhibit kinking of the tube 12. Thus, the flexibility and deflection characteristics of the second embodiment of the present invention remain similar to the characteristics of the prior art strain relief device 13 when used without a redundant bond (i.e., in the manner as is shown in FIG. 1).

Figure 5:
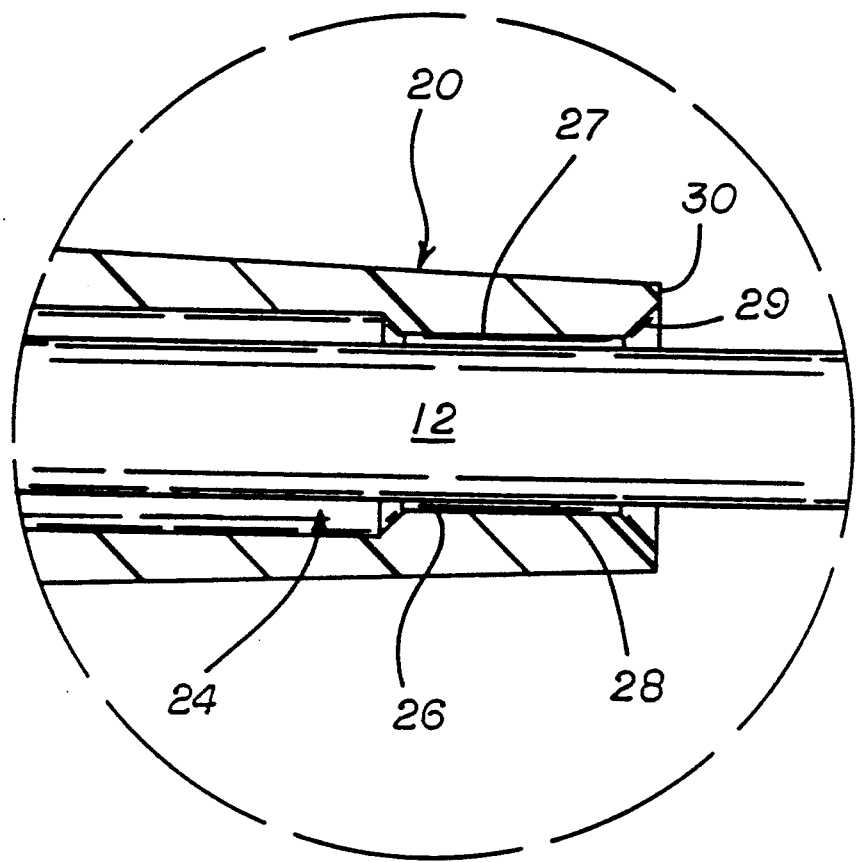
FIG. 5 is an enlarged view of area labeled "V" as shown is FIG. 4.

As shown in FIGS. 4 and 5, the strain relief device 20 of the second embodiment of the present invention is preferably formed of a polyurethane material having a durometer hardness similar to that of the prior art strain relief device 13 (i.e., a durometer hardness somewhere between the durometer hardness of the hub 11 and the tube 12). The device 20 is formed in a conical elongated shape, the proximal portion 21 having the largest diameter, with the diameter decreasing in the direction of the central portion 22 and the distal portion 23 thereof.

The device 20 includes a lumen 24 which passes through its entire length. The lumen 24 forms generally three sections of varying diameters; a proximal section 25 of a diameter which is substantially equal to the outer diameter of the nose portion 33 of hub 11 which is to be inserted therein; a central section 26 which is of a diameter substantially larger than the outer diameter of the tube 12; and, a distal section 27 having a diameter which is only slightly larger than the outer diameter of tube 12.

The size of the distal lumen section 27 is predetermined to form an annular shaped cavity 28 between its inner surface and the outer surface of the tube 12 when tube 12 is inserted therein. If desired, a distal end 30 of the distal section 27 of the lumen 24 may be formed into a funnel shaped opening 29 to aid in dispersement of bonding material in the manner as will be explained below.

The geometry of the annular cavity 28 is designed to allow for a bond between the tube 12 and the distal section 27 of the lumen 24 such that the axial pull to separation force resistible between the hub 11 and the tube 12 will be on the order of the axial pull to separation force of the tube 12 itself, which is the ultimate limiting factor of the strength of the catheter 10.

Figure 6:
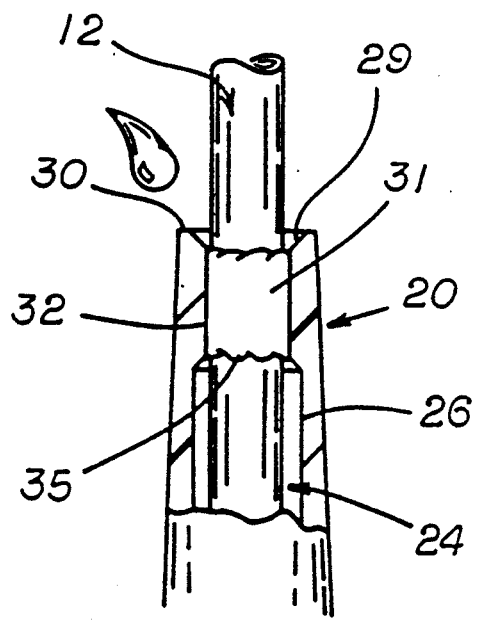
FIG. 6 is a partial cross-sectional view, showing the capillary flow pattern of bonding material between the catheter tube and the strain relief device of the second preferred embodiment of the invention as shown in FIG. 5, the catheter and the bonding material being shown in perspective and the strain relief device being shown in partial cross-section.

Also, the geometry of annular cavity 28 is designed to correlate with the viscosity of the bonding material 31 (as shown in FIG. 6) so that capillary forces resulting from the placement of bonding material 31 into the cavity 28 will pull the bonding material into a complete, even, uniform bonding pattern which at least forms a bond having a radially symmetrical distal end surface about the tube 12 at the distal end 30 of device 20 and which preferably entirely fills and corresponds precisely with the geometry of the annular cavity 28.

Further, the overall geometry of the device 20 and its lumen 24 is designed so that deflection and flexibility characteristics remain the same or similar to predetermined characteristics for similar type strain relief devices (such as device 13 as shown in FIG. 1). These flexibility and deflection characteristics are important to maintain in order to avoid abrupt curvature changes (kinking) of the tube and to insure predictable and uniform (or uniformly changing) curvatures along the entire hub/tube junction 14 during its subjection to bending forces.

The cavity 28 is properly referred to as a "wicking cavity" since it in effect is capable of pulling bonding material thereinto through wicking or capillary forces to completely and evenly fill the cavity 28 to form a uniform bilaterally symmetrical bond.

As best shown in FIGS. 5 and 6, the geometry of cavity 28 is defined by inner surface 32 of the distal section 27 of the lumen 24, and the outer surface of the portion of tube 12 directly most adjacent thereto. The funnel 29 functions to allow placement of bonding material 31 thereinto and allows the bonding material to flow at least partially around the tube 12 before entering cavity 28. The bonding material 31 is drawn into cavity 28 by capillary action and is pulled in all directions until it completely and uniformly fills the cavity 28. Since the central section 26 of the lumen 24 is of a substantially larger diameter than that of distal section 27 which forms cavity 28, capillary forces tend to inhibit any bonding material 31 from entering into the central section 26 of the lumen 24.

The first preferred embodiment of the present invention as shown in FIG. 3 may be manufactured in the following manner.

First, a prior art type catheter 10 is constructed by forming a tube 12 and inserting the proximal end thereof into a hub mold a sufficient distance to allow molten plastic to be injected thereinto. The molten plastic surrounds the portion of the tube 12 located therein and forms a bond between the hub 11 and the tube 12.

Once the prior art catheter 10 is completely formed, a bonding material such as a solvent may be placed on nose portion 33 of the hub 11, and the prior art type strain relief device 13 is placed thereabout, such as by inserting the device 13 over tube 12 and sliding it down to the hub 11 until the proximal portion thereof is forced over the nose 33 with the solvent forming a permanent bond therebetween.

As can be readily seen, the first embodiment of the present invention can be formed in an identical manner as the prior art, if desired, except that once the prior art strain relief device 13 is in place, the present invention manufacturing process further includes the step of forming a bond, such as by introducing a bonding material 18, into the distal end of lumen 15 of the strain relief device 13 to form the redundant bond 19 between the strain relief device and the tube 12.

The second preferred embodiment of the present invention is also manufactured in a manner similar to the prior art device as shown in FIG. 1, except that a strain relief device such as device 20 as shown in FIG. 4 is inserted over the tube 12 and permanently bonded to the nose 33 of hub 11. Thereafter, bonding material 31 can be placed in the funnel shaped opening 29 (if present, or directly into cavity 28 if not) and allowed to flow around the catheter tube 12 and drawn into the wicking cavity 28 by capillary forces. Capillary forces then continue to cause bonding material 31 to spread uniformly and evenly around tube 12 to form a bilaterally symmetrical redundant bond 34 between tube 12 and distal section 27 of the strain relief device 20.

Due to the enlarged diameter of the central section 26 of lumen 24, the bonding material 31 is held by capillary action in the cavity 28 and inhibited from passing into the central section 26, thus insuring the desired uniform annular shape of redundant bond 34.

It is anticipated that the geometry of the annular cavity 28 will need to be adjusted according to the viscosity and strength of the bonding material used. For example, in the second preferred embodiment of the invention as shown in FIGS. 4–6, when a solvent such as THF is used, it is anticipated that the diameter of the distal section 27 of the lumen 24 be sized to approximately two thousandths of an inch larger than the maximum anticipated diameter of the catheter tube 12. Therefore, in the case of a specific size of catheter 10, such as a catheter of 2.5 French size, having a tube 12 of approximately thirty-two thousandths plus or minus two thousandths of an inch in diameter, the diameter of the distal section 27 of the lumen 24 of the strain relief device 20 would preferably be formed to approximately thirty-six thousandths of an inch. This would insure that a spacing always existed between the catheter tube 12 and the distal section 27 of at least one thousandths of an inch on each side, yet never more than three thousandths of an inch. This would insure good capillary action between the cavity and the THF.

The length of cavity 28 along distal section 27 of the lumen 24, for a 2.5 French size catheter 10 should be in the range of twenty to sixty thousandths of an inch when using a solvent bonding material in order to insure sufficient bond strength. It is important to understand that the length of cavity 28 should be limited to only the distal portion 23 of the device 20 in order to avoid any negative effect on the flexibility and deflection characteristics thereof due to the presence of bond 34. Further, when using a solvent bonding material, the length of bond cavity 28 must also be limited in order to avoid entrapment of solvent in a manner which prevents proper evaporation (called "flashing") of components of the solvent in the bonding process. Otherwise, the excessive length of cavity 28 may prevent proper "flashing" and result in the trapped unevaporated solvent components degradating the plastic of the catheter tube 12 and device 20, inevitably compromising the structural integrity of the catheter 10.

The redundant bond 19 of the first preferred embodiment of the invention (as shown in FIG. 3) significantly increases pull to separation forces required to separate hub/tube junction 14 over prior art catheter designs (such as exemplified in FIG. 1). Similarly, substantially greater pull to separation forces are achieved with the second preferred embodiment of the invention (as shown in FIGS. 4–6).

The flexibility and deflection characteristics of the strain relief device 20 of the second embodiment of the present invention remain substantially similar to the characteristics of the prior art strain relief device 13 (without a redundant bond as shown in FIG. 1). This is due to the fact that the strain relief device 20 is formed with the central section 26 of the lumen 24 thereof of a substantially increased diameter over the diameter of lumen 15 of the prior art device 13. The enlarged diameter of the central section 26 of device 20, combined with the design of the distal portion 23 thereof, and the inclusion of redundant bond 34, have a net result of generating flexibility and deflection characteristics in the strain relief device 20 which are similar to the deflection and flexibility characteristics of the prior art strain relief device 13 (as used in FIG. 1).

It should be understood that the respective diameters of central section 26 and distal section 27 of lumen 24 perform two functions; first, to form a wicking cavity 28 which draws bonding material 31 into a uniform annular bonding pattern 34, (which is prevented through capillary action from moving into the central section 26); and second, to generate flexibility and deflection characteristics similar to those demonstrated by the prior art strain relief device 13 (as shown in FIG. 1).

It will be apparent from the foregoing that, while the particular shown embodiments of the invention relate to use of the invention with catheters, various other general uses of the invention in conjunction with other types of tubular devices are anticipated, including modifications to the particularly illustrated embodiments, without departing from the spirit and scope of the invention. Accordingly, it is not intended that the invention be limited in any manner, except as by the appended claims.

We claim:

1. A device for relieving strain concentration at a junction between a rigid member and a flexible member of a medical device, said strain relief device comprising:
   a strain relief body having a proximal portion, a central portion, and a distal portion, said strain relief body forming a lumen therethrough, and the junction between the rigid member and the flexible member being positioned within said lumen,
   means attaching said proximal portion of said strain relief body to the rigid member,
   means attaching said distal portion of said strain relief body to the flexible member, and including a wicking cavity located between said distal portion and the flexible member, said wicking cavity including means for encouraging wicking of a bonding material therein, and said means attaching said distal portion of said strain relief body to the flexible member further including bonding material in said wicking cavity, and
   means for discouraging wicking in said central portion,
   whereby, said device inhibits strain concentrations due to lateral-type forces which tend to bend the flexible member at an angle relative to the rigid member, and due to axial pull forces which tend to separate the flexible member from the rigid member.

2. A strain relief device according to claim 1 wherein said means for discouraging wicking further includes a variation in the diameter of said lumen between said distal portion and said central portion.

3. A device according to claim 1 wherein said lumen is formed of a proximal section, a central section, and a distal section, said distal section being attachable to the flexible portion of the elongate member and said proximal section being attachable to the rigid portion of the elongate member.

4. A device according to claim 3 wherein said distal section of said lumen is formed of a diameter which is less than the diameter of said central section of said lumen.

5. A strain relief device according to claim 1 wherein said bonding material forms a bi-laterally symmetrical bond between said distal section of said lumen and the flexible portion of the elongate member.

6. A strain relief device according to claim 5 wherein said bonding material is a solvent.

7. A strain relief device according to claim 6 wherein said elongate member is a catheter and wherein said rigid portion is a catheter hub and said relatively flexible portion is a catheter tube.

8. A strain relief device according to claim 1 wherein said distal section of said lumen further includes a distal end, said distal end being conical in shape and forming a bonding material dispersion funnel which is in fluid flow connection with said wicking cavity and which aids in even dispersion of bonding material into said wicking cavity.

9. A strain relief device according to claim 8 wherein said dispersion funnel of said distal end of said lumen aids in bonding material flow around the flexible portion of the elongate member.

10. A strain relief device according to claim 8 wherein said bonding material forms a bond which is uniformly symmetrical about the tube end distal and of said device.

11. A strain relief device according to claim 1 wherein said central section of said lumen includes means for inhibiting the flow of bonding material from said distal section into said central section.

12. A strain relief device according to claim 1 wherein said means at said distal portion for attaching the flexible portion of the elongate member to said body includes bonding material, and further includes means for dispersing said bonding material into a controlled bonding pattern between said lumen and the flexible portion of the elongate member.

13. A strain relief device according to claim 1 wherein said means for attaching said distal portion of said lumen to the flexible portion of the elongate member includes means for forming a bi-laterally symmetrical bond between said distal portion of said body and the flexible portion of the elongate member.

14. A method of forming a strain relief device about a junction between a relatively rigid portion and a relatively flexible portion of an elongate member, said method comprising the steps of:

forming a strain relief device which includes a lumen therethrough, the lumen having a distal section, a central section, and a proximal section, the diameter of the distal section being smaller than the diameter of the central section.

inserting the elongate member through the lumen of the strain relief device until the junction between the relatively rigid portion and the relatively flexible portion of the elongate member rests within the lumen, attaching the proximal section of the lumen to the relatively rigid portion of the elongate member, and attaching the distal section of the lumen to the relatively flexible portion of the elongate member by permanently bonding the distal section to the relatively flexible portion by inserting bonding material into a cavity formed by the distal section and the relatively flexible portion and evenly distributing the bonding material therein through capillary action, and discouraging bonding material from passing into the central section of the lumen through the aid of capillary action by inserting a bonding material into the cavity which is of a viscosity which will allow it to disperse by capillary action within the cavity, yet be inhibited in its dispersion in the central section of the lumen by capillary action due to the variation in the diameter of the lumen between the distal section and the central section thereof.

15. A method according to claim 14 wherein said step of permanently bonding the distal section of the lumen to the relatively flexible portion of the elongate member includes forming a bond having at least a radially symmetrical distal end surface which is formed about a distal end of the distal section of the device.

16. A method according to claim 14 wherein said step of forming a controlled bond pattern further includes forming a bi-laterally symmetrical bond pattern.

17. A method according to claim 14 wherein said step of inserting bonding material into the cavity includes inserting a solvent into the cavity.

18. A method according to claim 14 wherein said step of forming a cavity includes forming the distal section of the lumen to a diameter of approximately two thousandths of an inch greater than the outer diameter of the relatively flexible portion of the elongate member.

19. A method according to claim 14 wherein the elongate member is a catheter, the relatively rigid portion of the elongate member being a catheter hub and the relatively flexible portion of the elongate member being a catheter tube, and the steps of attaching the proximal and distal sections of the lumen to the elongate member includes attaching the proximal section of the lumen to the hub and attaching the distal section of the lumen to the tube.

* * * * *